United States Patent [19]

Kosaka

[11] Patent Number: 5,083,014
[45] Date of Patent: Jan. 21, 1992

[54] AUTOMATIC FOCAL-POINT ADJUSTMENT METHOD IN FLOW IMAGING CYTOMETER

[75] Inventor: Tokihiro Kosaka, Hyogo, Japan

[73] Assignee: TOA Medical Electronics Co., Ltd., Kobe, Japan

[21] Appl. No.: 633,783

[22] Filed: Dec. 26, 1990

[30] Foreign Application Priority Data

Jul. 24, 1990 [JP] Japan .................. 2-195934

[51] Int. Cl.$^5$ ............................................. G01J 1/20
[52] U.S. Cl. .................. 250/201.7; 250/573
[58] Field of Search ............................. 250/201.7, 573; 356/335, 337

[56] References Cited

U.S. PATENT DOCUMENTS 4,519,087  5/1985  Deindoerfer .................. 377/10

Primary Examiner—David C. Nelms
Assistant Examiner—Teresa Davenport
Attorney, Agent, or Firm—Pearne, Gordon, McCoy & Granger

[57] ABSTRACT

A flow imaging cytometer for imaging the dimensions and shapes of particle components in a flow of a specimen solution employs a separate control solution, which is for managing precision, containing standard particles. A method of adjusting focal point with respect to the specimen flow includes steps of imaging the standard particles in the control solution, calculating an evaluation parameter which represents the definition of the image, and moving the flow cell or associated optical system so as to maximize the value of this parameter.

6 Claims, 7 Drawing Sheets

Fig. 1 (a) ORIGINAL IMAGE DATA

Fig. 1 (b) SOBEL OPERATOR

HORIZONTAL DIRECTION

VERTICAL DIRECTION

Fig. 1 (c) LAPLACIAN OPERATORS (c-1)

(c-2)

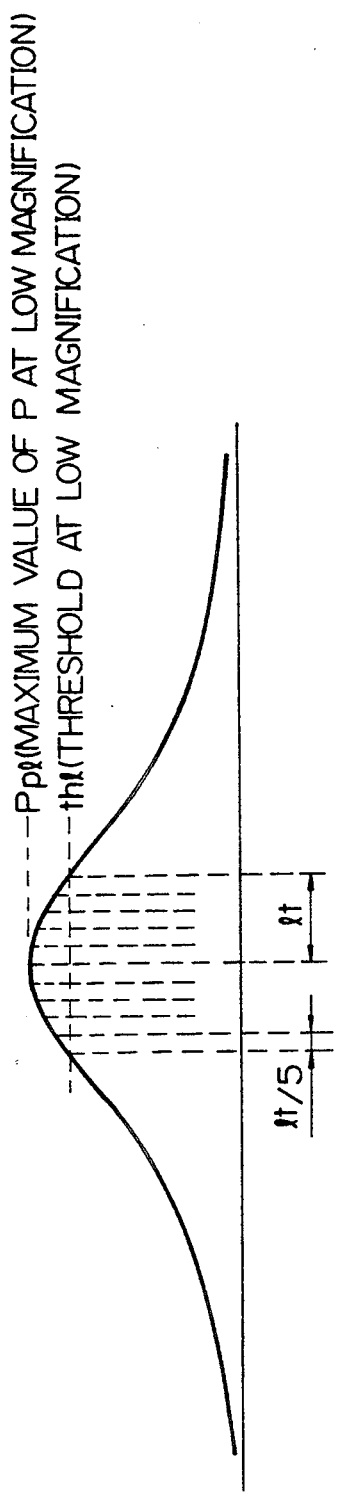

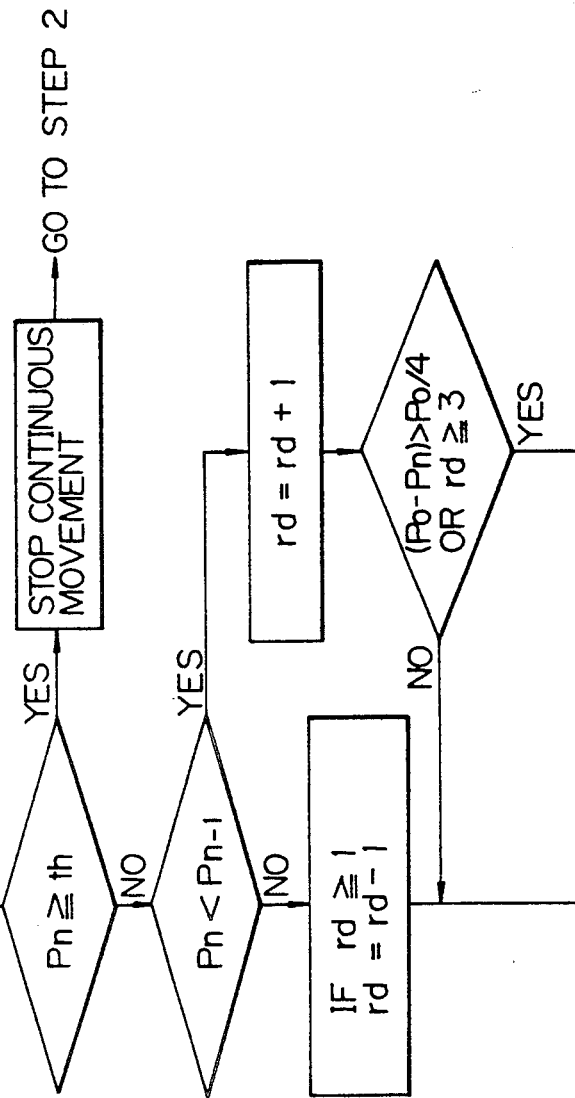

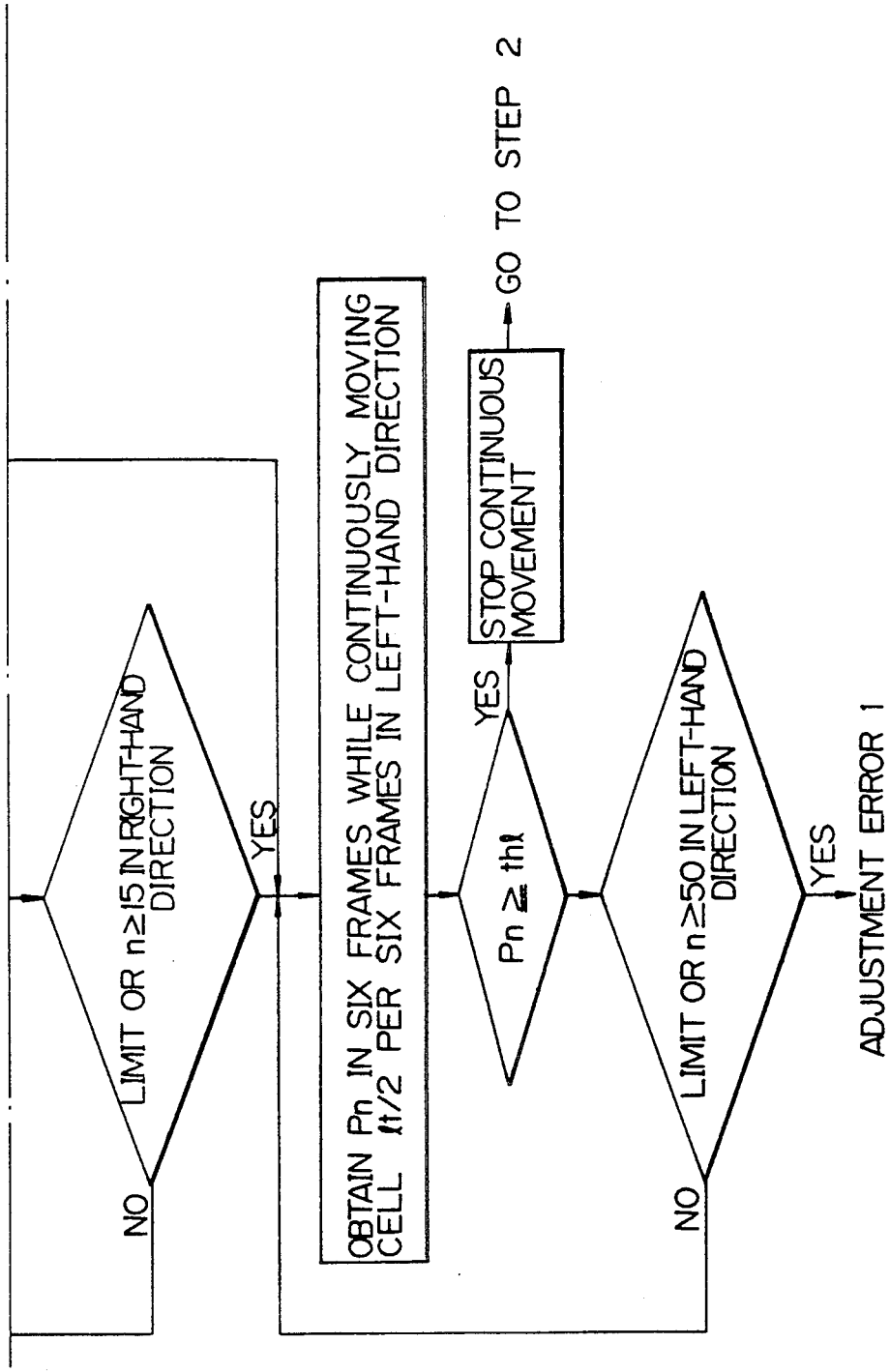

AUTOMATIC FOCAL-POINT ADJUSTMENT METHOD IN FLOW IMAGING CYTOMETER

BACKGROUND OF THE INVENTION

1. Field of the Invention

This invention relates to flow imaging cytometry in which a specimen such a blood or urine suitably stained is introduced to a flow cell to form a flat, sheathed flow within the cell, the sheathed flow zone is irradiated with strobe light, and a cell image obtained by a video camera is analyzed by image processor. More particularly, the invention relates to an automatic focal-point adjustment method used in such flow imaging cytometry.

2. Description of the Prior Art

A cell analyzing apparatus for imaging cells flowing in the form of a flat, sheathed stream and automatically classifying and counting the cells utilizing image processing technology has been disclosed in the specifications of Japanese Patent Application Laid-Open (KOKAI) No. 57-500995 (1982) and U.S. Pat. No. 4,338,024.

An automatic focusing method is also known in which the image of an object produced by a lens is formed in an automatically focused state at a prescribed position. For example, the specification of Japanese Patent Publication (KOKOKU) No. 42-14096 (1967) describes a technique which uses an array of photoelectric elements having a very small surface area. Differences in output between mutually adjacent ones of the photoelectric elements are totaled and the total value is maximized when focusing is achieved. This technique detects the maximum point. Also known are various evaluation relations for evaluating the definition of an image. For example, the specification of Japanese Patent Publication (KOKOKU) No. 58-41485 (1983) describes making use of a mean-square function.

Since cameras such as still cameras or video cameras deal with images in which there is almost no change from one frame to the next, performing a focal-point adjustment while moving lenses or a group of image pickup elements in very small amounts is comparatively easy. However, in capturing a cell image or the like in flow imaging cytometry, the image changes every frame (every 1/30 of a second), and the positions and number of cells that appear in each frame change vastly. Consequently, performing focusing by comparing the same image from one frame to the next while moving a lens or the like in minute increments is difficult. Accordingly, automatic focusing is not easy to achieve.

SUMMARY OF THE INVENTION

An object of the present invention is to provide a efficient automatic focal-point adjustment method used in flow imaging cytometry and adapted to solve the aforementioned problems encountered in cell analysis.

According to the present invention, the foregoing object is attained by providing an automatic focal-point adjustment method in a flow imaging cytometer in which a specimen solution containing particle components such as cells is made to flow as a flat specimen solution having a sheathing liquid as an outer layer thereof along a flat flow path within a flow cell, light irradiating means and imaging means are arranged on opposite sides of the flow cell, a still image of the specimen solution is captured and the image is subjected to image processing, whereby analysis such as classification and enumeration of the particle components contained in the specimen solution is performed. The automatic focal-point adjustment method is characterized by passing a control solution, which contains particles of uniform dimensions and shape, through the flow cell as a dummy solution, moving the position of the flow cell or of an optical measuring component by a fine adjustment device such as a stepping motor, continuously capturing the control solution during such movement and calculating evaluation parameters which accurately represent the definition of the images obtained, and adjusting the position of the flow cell or of the optical measuring component in such a manner that a value of an evaluation parameter attains a maximum value, thereby eventually achieving focal-point adjustment.

BRIEF DESCRIPTION OF THE DRAWINGS

The figures are views for describing an embodiment of the present invention, in which:

FIGS. 1(a) and (b) illustrate examples of original image data and Sobel operators and FIG. 1(c) Laplacian operators when obtaining evaluation parameters of an image;

FIG. 2 is an example of an evaluation parameter curve;

FIGS. 7A and 7B show a basic flowchart of coarse focus adjustment.

DESCRIPTION OF THE PREFERRED EMBODIMENT

Figure 3:
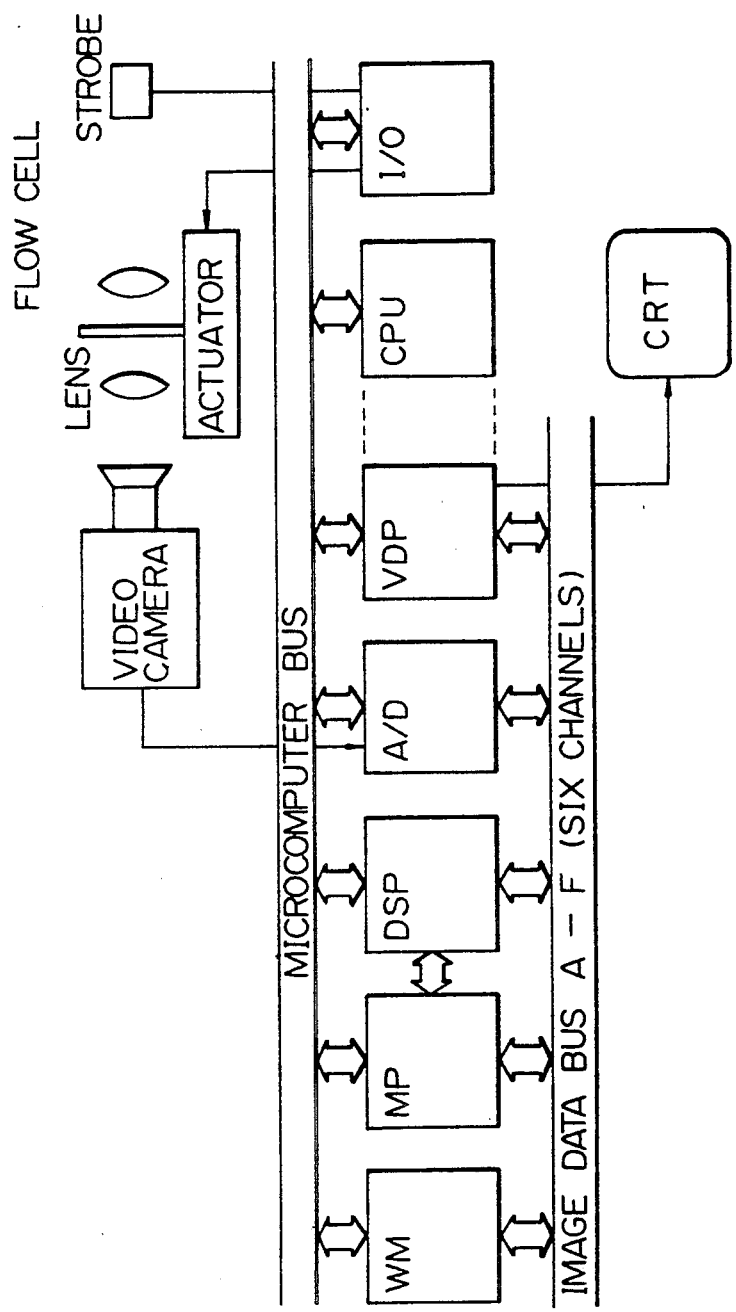
FIG. 3 is a block diagram showing an image processing system for flow imaging cytometry.

An embodiment of the present invention will now be described in detail with reference to the accompanying drawings.

In flow imaging cytometry according to the present invention, a cumulative value obtained by totaling differential values at local areas of an image over the entire frame of the image is used as an evaluation parameter representing the degree of focusing of the image, such as the image of a cell. Sobel operators shown in FIG. 1(b) are employed as an example of operators for obtaining a differential value in a local area of the image. As a coefficient corresponding to each item of data of $3 \times 3 = 9$ pixels surrounding a pixel of interest $x_{ij}$ shown in FIG. 1(a), use is made of a new value corresponding to the pixel of interest $x_{ij}$ using the values of nine pixels obtained by multiplying the above-mentioned pixel by horizontal and vertical Sobel operators. This is referred to as a $3 \times 3$ convolution. Such new values are calculated with regard to all pixels in the entire image frame.

More specifically, new values are calculated in accordance with the following as differentiated values in the horizontal and vertical directions of the pixel of interest:

$$Sbx_{ij} = x_{{i-1} \atop {j-1}} + 2x_{i \atop j-1} + x_{{i+1} \atop {j-1}} - x_{{i-1} \atop {j+1}} - 2x_{i \atop j+1} - x_{{i+1} \atop {j+1}} \quad (1)$$

$$Sby_{ij} = x_{{i-1} \atop {j-1}} + 2x_{{i-1} \atop j} + x_{{i-1} \atop {j+1}} - x_{{i+1} \atop {j-1}} - 2x_{{i+1} \atop j} - x_{{i+1} \atop {j+1}} \quad (2)$$

In a background portion where particles do not appear the new value is approximately zero. However, when a particle enters the image frame, the calculated value at the contour thereof becomes larger in proportion to contrast as focusing is performed. Accordingly, a value obtained by accumulating such calculated values over the entire image frame can be utilized as an evaluation parameter indicating the degree of focusing.

According to the present invention, a solution containing control particles for precision management in which particles are uniform in dimensions and shape is introduced to a flow cell, and focusing is performed by processing the image in which the particles appear, thereby raising the precision of classification and analysis of a specimen containing a wide variety of particle components. In this case, the number of particles which appear in one frame will be only several tens at low magnification and several at high magnification. As a result, the cumulative differential value for one frame will exhibit a large statistical variance when compared with other frames.

Accordingly, a value obtained by totaling the cumulative differential value for one frame over several frames or several tens of frames is adopted as the final evaluation parameter, denoted by P. This parameter P is given by the following formula:

$$P = \sum_{frame} \sum_{ij} \{(Sbx)^2/k + (Sby)^2/k\} \quad (3)$$

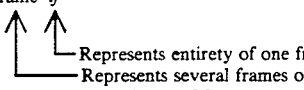

Represents entirety of one frame
Represents several frames or several tens of frames In the above formula for calculating the evaluation parameter, taking the square of Sbx, Sby is effective in order to raise the sensitivity and Q value of the degree of focusing. The coefficient k is given a value which will prevent overflow.

Another method of obtaining the evaluation parameter P is to use Laplacian operators. Two types of Laplacian operators (c-1), (c-2) are illustrated in FIG. 1(c). When the Laplacian operator (c-1) is used, a 3×3 convolution takes on the following value:

$$lapx_{ij} = 4x_{i\atop j} - x_{i-1\atop j} - x_{i\atop j+1} - x_{i\atop j-1} - x_{i+1\atop j} \quad (4)$$

When the Laplacian operator (c-2) is used, we have $$lapx_{ij} = 8x_{i\atop j} - x_{i-1\atop j-1} - x_{i-1\atop j} - x_{i-1\atop j+1} - x_{i\atop j-1} - x_{i\atop j+1} - \quad (5)$$

$$x_{i+1\atop j-1} - x_{i+1\atop j} - x_{i+1\atop j+1}$$

If the evaluation parameter P is obtained using Equation (4) or (5), P will be expressed by either of the following:

$$P = \sum_{frame} \sum_{ij} |lapx_{ij}|/h \quad (6)$$

$$P = \sum_{frame} \sum_{ij} (lpx_{ij})^2/h \quad (7)$$

where h is a constant.

In accordance with the Sobel method, the differential value $Sbx_{ij}$ which uses the horizontal operator and the differential value $Sby_{ij}$ which uses the vertical operator are obtained, and the evaluation parameter P is calculated using Equation (3). With the Laplacian method, however, it will be noted that one step of the calculations can be omitted.

Figure 4:
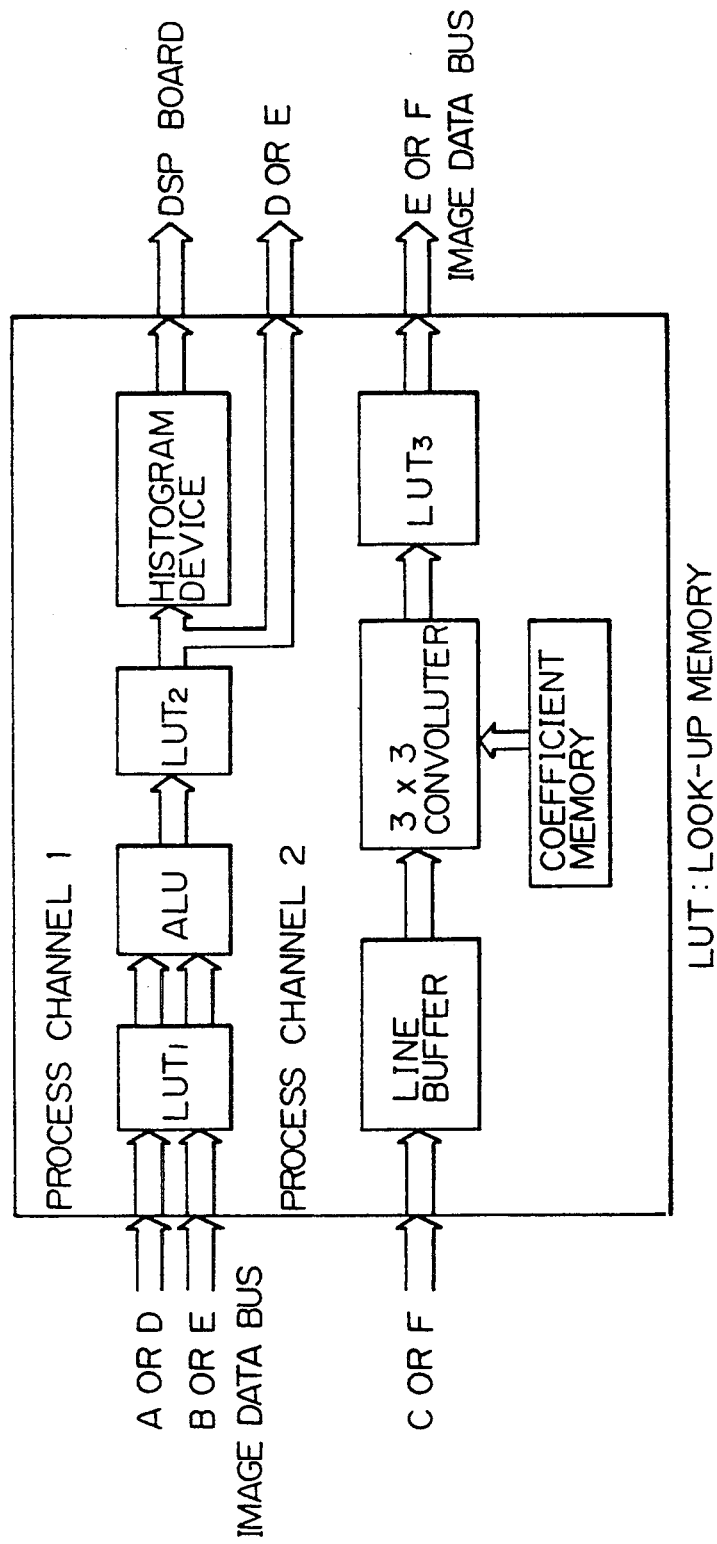
FIG. 4 is a block diagram of a morphology processor board ideal for use in the system of FIG. 3.

The above-mentioned evaluation parameter is obtained by real-time processing of the image data using an image processor with which the cytometer is furnished. When the evaluation parameter is plotted while finely moving the flow cell or lens with regard to one frame, a curve of the kind shown in FIG. 2 is obtained. The point at which the maximum value is obtained is the position at which focusing is achieved. An evaluation parameter according to Equation (3) is obtained using an image processor shown in FIG. 3. An example of the circuitry of an image processor board forming the nucleus of FIG. 3 is illustrated in FIG. 4. A morphology processor board is a board on which general functions necessary for processing a cell image are mounted; the board is not specially mounted in order to focus an image. Illustrated below is a method of obtaining evaluation parameters of a plurality of frames in which one field (1/60 of a second) is adopted as one step.

Figure 5:
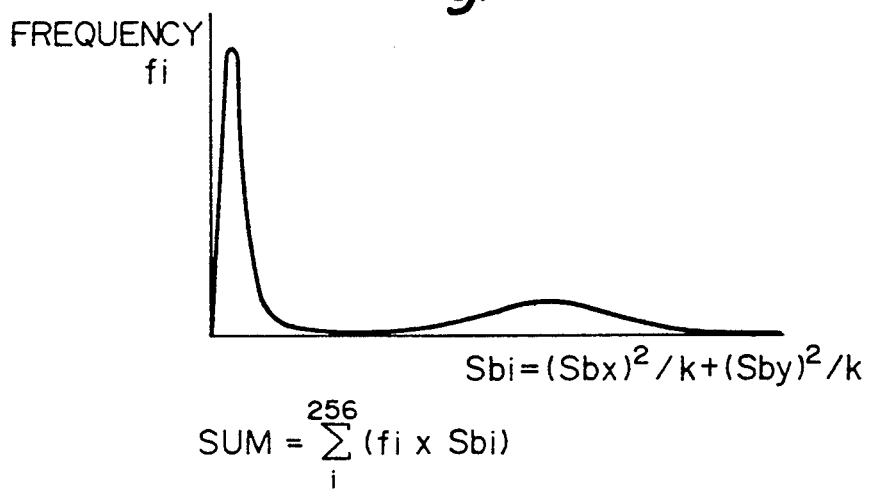
FIG. 5 is an example of a histogram of an evaluation parameter.

In FIGS. 3 and 4, (i) data indicative of the frame of an odd-numbered field A/D-converted by an A/D board, namely a video signal analog/digital conversion board, is inputted to a process channel 2 of a morphology processor board MP via an image data bus C, a differential value $(Sbx)^2/k$ in the horizontal direction is obtained in real-time, and this data is stored in a working memory WM via an image data bus E; (ii) data indicative of the frame of an even-numbered field A/D-converted by the A/D board is inputted to the process channel 2 of the morphology processor board MP via the image data bus C, a differential value $(Sby)^2/k$ in the vertical direction is obtained, this data is inputted to a process channel 1 via the image data bus E, the data indicative of $(Sbx)^2/k$ stored in the working memory is read out to the image bus simultaneously, the data is added to an ALU, and a histogram of the added values is prepared in real-time by a histogramer; and (iii) the results of the histogram of the kind shown in FIG. 5 prepared in step (ii) are accumulated by a digital signal processor DSP on the digital signal processor board, and an evaluation parameter for one frame is obtained.

If a general-purpose high-speed microprocessor or digital signal processor is used, calculating the evaluation parameter for one frame will take one second assuming that one frame is composed of 256×256 pixels. Therefore, about 20 seconds will be required to obtain evaluation parameters for 20 frames. In actuality, however, a longer time is required since focus adjustment is performed while moving the lenses or flow cell. On the other hand, if an evaluation parameter is obtained in real-time with respect to one frame which appears every 1/30 of a second, 20/30 of a second will be required to obtain evaluation parameters for 20 frames. Ideally, therefore, an evaluation value for focusing should be obtained using a digital filter, namely a 3×3 convolution filter, described below, which incorporates a high-speed multiplier and a high-speed cumulative adder. At the same time, processing similar to that of step (i) is executed with regard to the next frame in conjunction with step (iii). (iv) Processing similar to that of step (ii) is executed with regard to the next frame. (v) After processing similar to that of step (iii) is executed with regard to the next frame, the evaluation parameter of the initial frame and the evaluation parameter of the next frame are added. At the same time, processing similar to that of step (i) is executed with regard to the next frame. Thereafter, processing is applied to successive frames one after another in the same manner.

Since one frame is the sum of the odd-numbered and even-number fields, the differential values Sbx, Sby of Equation (3) can be obtained in real-time by an FIR filter used as the 3×3 convoluter (FIG. 4) of process channel 2. Furthermore, processing for squaring both differential values and then multiplying them by 1/k can be performed in real-time by a look-up table $LUT_3$.

Figure 6:
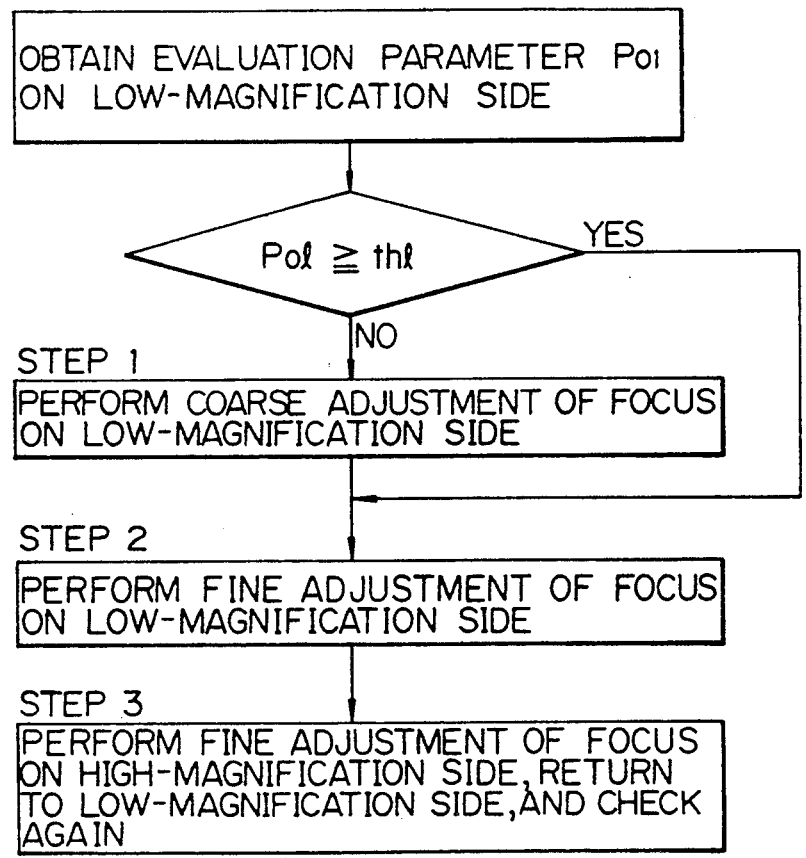
FIG. 6 is a basic flowchart of focus adjustment.

An actual focal-point adjustment algorithm using the evaluation parameter P will now be described. A system whose basic aim is to perform accurate focal-point adjustment in an efficient manner and which requires imaging while changing magnification will be described in accordance with FIG. 6 showing a focusing flowchart. Focusing in the present invention is divided into two stages, namely, a coarse adjustment step and a fine adjustment step.

First, a control solution is passed through a flow cell and imaged by a video camera, and an initial value $P_{ol}$ of the evaluation parameter of the image on the low-magnification mode is obtained. In this case, cumulative differentiated values for every several frames are obtained while the flow cell or lens is finely adjusted. When fine adjustment of focus is performed, the speed at which the flow cell or lens is moved cannot be made very high, though the speed of movement can be raised at coarse adjustment of focus. When it is determined that an image is too far out of focus, namely when the relation $P_{ol} < th_l$ holds with regard to a threshold $th_l$ that gives the boundary between a coarse-adjustment region and a fine-adjustment region, it is required to bring adjustment to the fine-adjustment region much more speedily by following Step 1, which constitutes performing coarse adjustment at a high speed of flow cell or lens movement.

The threshold value $th_l$ is decided as follows: If the apparatus to be focused is undergoing the focus adjustment for the first time, the first step is to obtain the mean value and mean rate of fluctuation of the evaluation parameters which prevail when the temperatures and sheath pressures of several sets of the same model apparatus already adjusted are varied to the maximum limit within a practical range. A value obtained by multiplying this mean value by 0.9, for example, is adopted as the initial value of $th_l$. Once an apparatus has already had its focus adjusted, the value of $th_l$ when the apparatus is readjusted will be obtained in accordance with the following equation using an evaluation parameter value $P_{pl}$ that prevailed at the initial adjustment or immediately preceding adjustment:

$$th_l = P_{pl}(1 - \text{mean fluctuation rate}) \times 0.9.$$

By thus deciding $th_l$, focus readjustment of an apparatus already focused once starts, in most cases, from the fine adjustment of Step 2, with coarse adjustment being skipped.

The focal-point adjustment process of the present invention, which is premised on the foregoing, is summed up by the flowchart of FIG. 6. Each procedure will now be described.

(1) The control solution is passed through the flow cell.

(2) The initial value $P_{ol}$ of the evaluation parameter on the low-magnification mode is obtained.

(3) The initial value $P_{ol}$ of the evaluation parameter and a predetermined value $th_l$ are compared. If $P_{ol} < th_l$ holds, the program proceeds to Step 1; if $P_{ol} \geq th_l$ holds, the program skips Step 1 and proceeds to Step 2.

(4) Step 1: Coarse adjustment of focus on low-magnification mode

The evaluation parameter $P_n$ is obtained while moving the flow cell, and the program proceeds to Step 2 if $P_n \geq th_l$ holds.

(5) Step 2: Fine adjustment of focus on low-magnification mode

The evaluation parameter $P_n$ is obtained while moving the flow cell, and the flow cell is moved to a position at which the evaluation parameter $P_n$ is maximized.

(6) Step 3: Fine adjustment of focus on high-magnification mode, and verification FIG. 7 illustrates an adjustment algorithm to which the foregoing adjustment procedure is capable of being applied through Steps 1, 2, 3. This deals also with an anomaly which occurs when an adjustment error is determined with regard to an image in which about 180 particles appear in six frames. The adjustment time required for Step 1 is 0.5–11 seconds.

Next, when the apparatus is slightly out of focus at low magnification, Step 2 is executed in the next procedure in the above-described adjustment algorithm. The time required for adjustment at Step 2 is 6–7 seconds.

Step 2 (Fine Adjustment): $P_o \geq th_l$ (1) $P_n$ for every six frames is obtained while moving the flow cell continuously lt/5 per six frames in the right-hand direction.

(2) If the relation $P_n < th_l$ is attained and $P_n$ is obtained for four or more points, then continuous movement in the right-hand direction is stopped.

(3) $P_n$ for every six frames is obtained while moving the flow cell continuously lt/5 per six frames in the left-hand direction in a manner similar to (1).

(4) If the relation $P_n < th_l$ is attained, then continuous movement in the left-hand direction is stopped.

(5) The value of P at each point obtained in (1) and (3) is subjected to smoothing processing and the amount of backlash is found. The point at which P is maximized is obtained.

(6) Upon taking backlash into consideration, the flow cell is moved to the point obtained in (5).

(7) The value of P in 30 frames at this position is obtained, and this value $P_{pl}$ and the position $P_{sl}$ are stored in memory.

(8) When $P_{pl}$ is smaller than a prescribed value $P_{pls}$, this is determined to be an adjustment error 2.

(9) The program proceeds to Step 3.

Next, following the focus adjustment on the low-magnification mode, Step 3, which is for a fine adjustment on the high-magnification mode, is executed through the following procedure:

Step 3: Fine Adjustment on High-Magnification Mode (1) Magnification is changed over from the low mode to the high mode, and 30 frames of $P_{oh}$ at the point adjusted on the low-magnification mode is obtained. (There are about 60 particles in 30 frames.)

(2) The relation $P_{oh} \geq th_h$ (the threshold on the high-magnification mode) is verified. If the relation $P_{oh} < th_h$ holds, then this is determined to be an adjustment error 3.

(3) $P_{nh}$ for every 30 frames is obtained while moving the flow cell continuously lth/5 per 30 frames in the right-hand direction.

(4) If the relation $P_{nh} < th_h$ is attained, then continuous movement is stopped.

(5) $P_{nh}$ for every 30 frames is obtained while moving the flow cell continuously lth/5 per 30 frames in the left-hand direction in a manner similar to (3).

(6) The value of P at each point obtained in (5) is subjected to smoothing processing and the point at which P is maximized is obtained.

(7) Upon taking backlash into consideration, the flow cell is moved to the point obtained in (6).

(8) The value of P in 90 frames at this position is obtained, and this value $P_{ph}$ and the position $P_{sh}$ are stored in memory.

(9) When $P_{ph}$ is smaller than a prescribed value $P_{phs}$, this is determined to be an adjustment error 4.

(10) Magnification is changed over from the high mode to the low mode, and 30 frames of $P_{ol}$ at the point adjusted on the high-magnification mode is obtained.

(11) $P_{ol}$ is compared with $P_{pl}$ obtained in Step 2 and an adjustment error 5 is determined when $P_{ol} < k_2 P_{pl}$ is found to hold ($k_2 = 0.8-0.85$).

(12) $P_{pl}$, $P_{ph}$, $P_{sl}$ and $P_{sh}$ which prevailed at the time of initial focus adjustment, two focus adjustments previously, the preceding focus adjustment and the present focus adjustment are compared and checked. When the differences exceed a prescribed value, an adjustment error 6 is determined.

The time required for the adjustment of Step 3 is 28-32 seconds.

The focus adjustment errors which occur in the foregoing steps can be considered to be caused by the following:

(1) Adjustment Error 1
a) an abnormality in the drive mechanism using the stepping motor;
b) the flow of control particles into the flow cell is not normal owing to an abnormality in the fluid system; and
c) clogging of a nozzle, etc.

(2) Adjustment Error 2
a) the position of the sample stream flowing through the flow cell has been disturbed;
b) the thickness of the sample stream flowing through the flow cell is excessive; and
c) the strobe has deteriorated.

(3) Adjustment Error 3
a) the position of the center of the sample stream flowing through the flow cell fluctuates in the thickness direction between the point at low magnification and another point at high magnification; and
b) the thickness of the sample stream flowing through the flow cell is excessive.

(4) Adjustment Error 4
a) the thickness of the sample stream flowing through the flow cell is excessive; and
b) the strobe has deteriorated.

(5) Adjustment Error 5
the position of the center of the sample stream flowing through the flow cell fluctuates in the thickness direction between the point at low magnification and the point at high magnification.

(6) Adjustment Error 6
a) the flow cell or lens drive unit is loose and worn;
b) the strobe has deteriorated;
c) dust has become attached to the lens, flow cell, etc.; and
d) the inner wall surface of the flow cell is contaminated.

In accordance with the adjustment method of the present invention, a still image of a specimen solution is captured every 1/30 of a second, and therefore identical frames do not occur. Evaluation parameters are obtained using these images that change from one instant to the next. Accordingly, though the evaluation parameters differ greatly from frame to frame, if a value obtained by adding up the evaluation parameters for a plurality of frames is adopted as the evaluation parameter, then the differences among a plurality of frames will be absorbed according to the rules of algebra, the characteristic features of the image are made to stand out and this is accurately reflected in the focused state of the cell image.

The value of the evaluation parameter is obtained in real-time while continuously moving the flow cell or lens, and the position at which this value is maximized is rapidly determined. In addition, the time required for adjustment can be curtailed first by coarse adjustment of focus at low magnification and then by fine adjustment of focus at high magnification.

If the maximum value of the evaluation parameter obtained whenever focal point is adjusted is stored in memory, any abnormality in the system can be discovered by monitoring and fluctuation in the stored value.

The present invention provides the following advantages:

(1) An evaluation parameter is obtained using images from a plurality of frames, during which time control particles for managing precision are used in focal-point adjustment, thereby making it possible to perform coarse adjustment and fine adjustment efficiently and precisely in a comparatively short period of time.

(2) A magnification change-over step is additionally provided, coarse adjustment of focus is performed first on the low-magnification mode where a large number of particles appear in one frame, and then fine (precise) adjustment of focus is performed on the high-magnification mode. This makes it possible to raise efficiency by a wide margin.

(3) The hardware of a cell analyzing system for processing cell images can be utilized as is. In other words, it is unnecessary to add separate hardware for adjusting focal point. As a result, the advantages mentioned above can be realized while minimizing cost.

As many apparently widely different embodiments of the present invention can be made without departing from the spirit and scope thereof, it is to be understood that the invention is not limited to the specific embodiments thereof except as defined in the appended claims.

What is claimed is:

1. In a flow imaging cytometer in which a specimen solution containing particle components is made to flow while sheathed by a sheathing liquid through a flat flow passageway of a flow cell, still images of the specimen solution are captured by light irradiating means and image pick-up means arranged on opposite sides of the flow cell, and analysis of particle components contained in the specimen solution is performed by image processing, a focal-point adjustment method comprising the steps of:

introducing a control solution, which contains particles of uniform dimensions and shape, to the flow cell;

capturing still images of the control solution while moving a component of an optical measuring system such as the flow cell;

calculating evaluation parameters which represent the definition of the still images; and performing focal-point adjustment with respect to specimen flow by adjusting the position of said component in such a manner that a value of an evaluation parameter is maximized.

2. The method according to claim 1 further comprising the steps of:

comparing an initial value $P_o$ of said evaluation parameter and a predetermined reference value th when the control solution is introduced to the flow cell;

obtaining an evaluation parameter $P_n$ and establishing a state in which $P_n > th$ holds by moving the flow cell when $P_o < th$ holds; and setting position by moving the flow cell to a position at which the evaluation parameter $P_n$ is maximized.

3. The method according to claim 1, further comprising the steps of:

comparing an initial value $P_o$ of said evaluation parameter and a predetermined reference value th when the control solution is introduced to the flow cell;

obtaining an evaluation parameter $P_n$ and establishing a state in which $P_n > th$ holds by moving a lens system of the flow cytometer when $P_o > th$ holds; and setting position by moving the lens system to a position at which the evaluation parameter $P_n$ is maximized.

4. The method according to any one of claims 1 through 3 further comprising the steps of:

first calculating said evaluation parameter on a low-magnification mode of the optical system; and when said evaluation parameter has been maximized, maximizing the evaluation parameter on a high-magnification mode of the optical system.

5. The method according to claim 4 further comprising the steps of:

storing a maximum value of said evaluation parameter; and sensing an abnormality of the measurement system by monitoring a fluctuation in the maximum value of said stored evaluation parameter.

6. The method according to any one of claims 1 through 3 further comprising the steps of:

storing a maximum value of said evaluation parameter; and sensing an abnormality of the measurement system by monitoring a fluctuation in the maximum value of said stored evaluation parameter.

* * * * *